(12) United States Patent
Kang et al.

(10) Patent No.: US 9,008,351 B2
(45) Date of Patent: Apr. 14, 2015

(54) METHOD AND APPARATUS FOR PROCESSING IMAGE, AND MEDICAL IMAGING SYSTEM EMPLOYING THE APPARATUS

(75) Inventors: Dong-goo Kang, Suwon-si (KR); Seok-min Han, Seongnam-si (KR); Seong-deok Lee, Seongnam-si (KR); Young-hun Sung, Hwaseong-si (KR); Sung-su Kim, Yongin-si (KR); Hyun-hwa Oh, Hwaseong-si (KR); Jae-hyun Kwon, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 86 days.

(21) Appl. No.: 13/813,007

(22) PCT Filed: Jul. 29, 2011

(86) PCT No.: PCT/KR2011/005631
§ 371 (c)(1),
(2), (4) Date: Jan. 29, 2013

(87) PCT Pub. No.: WO2012/015280
PCT Pub. Date: Feb. 2, 2012

(65) Prior Publication Data
US 2013/0129180 A1 May 23, 2013

(30) Foreign Application Priority Data

Jul. 29, 2010 (KR) .................. 10-2010-0073697

(51) Int. Cl.
*G06K 9/00* (2006.01)
*G06T 7/00* (2006.01)
*A61B 6/00* (2006.01)

(52) U.S. Cl.
CPC ............... *G06T 7/0012* (2013.01); *A61B 6/482* (2013.01); *A61B 6/502* (2013.01); *A61B 6/5217* (2013.01); *G06T 2207/10116* (2013.01); *G06T 2207/30068* (2013.01)

(58) Field of Classification Search
USPC ......... 382/100, 103, 106–107, 128, 134, 162, 382/168, 172–173, 181, 194, 232, 254, 258, 382/274, 276, 291, 305, 312; 600/476; 378/20, 21, 5, 53
See application file for complete search history.

(56) References Cited

U.S. PATENT DOCUMENTS

| 5,247,559 A | 9/1993 | Ohtsuchi et al. |
| 6,614,873 B1 | 9/2003 | Taylor et al. |

(Continued)

FOREIGN PATENT DOCUMENTS

| CN | 1738573 A | 2/2006 |
| CN | 101023875 A | 8/2007 |

(Continued)

OTHER PUBLICATIONS

International Search Report issued Apr. 26, 2012 in counterpart International Patent Application No. PCT/KR2011/005631 (3 pages, in English).

(Continued)

*Primary Examiner* — Seyed Azarian
(74) *Attorney, Agent, or Firm* — NSIP Law (57) ABSTRACT

A method of processing an image is provided. The method includes estimating a thickness of an object that includes at least two materials, from a radiation image taken with radiations of at least two energy bands; and generating an image by comparing the estimated thickness to a thickness of a local region and extracting a region of interest.

18 Claims, 6 Drawing Sheets

(56) References Cited

U.S. PATENT DOCUMENTS

| | | | |
|---|---|---|---|
| 6,674,835 B2* | 1/2004 | Kaufhold et al. | 378/53 |
| 7,873,198 B2* | 1/2011 | Shepherd et al. | 382/132 |
| 2004/0264627 A1* | 12/2004 | Besson | 378/5 |
| 2005/0187478 A1* | 8/2005 | Beaudry et al. | 600/476 |
| 2007/0092056 A1 | 4/2007 | Flohr et al. | |
| 2008/0167552 A1 | 7/2008 | Bouchevreau et al. | |
| 2010/0034348 A1* | 2/2010 | Yu | 378/20 |
| 2014/0232752 A1 | 8/2014 | Ren et al. | |

FOREIGN PATENT DOCUMENTS

| | | |
|---|---|---|
| JP | 63-247870 A | 10/1988 |
| JP | 5-99829 | 4/1993 |
| JP | 05-161631 A | 6/1993 |
| JP | 2002-530171 A | 9/2002 |
| JP | 2003-515376 | 5/2003 |
| JP | 2006-519625 | 8/2006 |
| JP | 2007-111525 | 5/2007 |
| JP | 2008-161690 A | 7/2008 |

OTHER PUBLICATIONS

Japanese Notice of Allowance issued on Mar. 28, 2014 in corresponding Japanese Application No. 2013-521719 (6 pages with English translation).

Chinese Office Action issued Jul. 17, 2014 in corresponding Chinese Application No. 201180037280.8 (12 pages with English translation).

* cited by examiner

METHOD AND APPARATUS FOR PROCESSING IMAGE, AND MEDICAL IMAGING SYSTEM EMPLOYING THE APPARATUS

CROSS-REFERENCE TO RELATED APPLICATION(S)

This application is a national stage of International Application No. PCT/KR2011/005631 filed Jul. 29, 2011, claiming priority based on Korean Patent Application No. 10-2010-0073697 filed Jul. 29, 2010, the contents of all of which are incorporated herein by reference in their entirety.

BACKGROUND

1. Field

The following description relates to a method and an apparatus for processing an image, and, for example, to a medical imaging system employing such an apparatus.

2. Description of Related Art

A radiation image, such as an X-ray image of a predetermined subject like the body of a patient, is obtained by the varying transmittance of X-ray through different types of materials and densities of the materials present in the body of the patient, as well as the energy band of the X-ray. As a result, sometimes, certain tissues or materials in a patient's body are not easily identified by using only one X-ray image. In particular, normal and abnormal tissues in a patient's body may not be easily identified from an X-ray image.

SUMMARY

In one general aspect, there is provided a method of processing an image involving: estimating a thickness of an object that includes at least two materials, from a radiation image taken with radiations of at least two energy bands; and generating an image by comparing the estimated thickness to a thickness of a local region and extracting a region of interest.

The region of interest may be an abnormal tissue.

The two materials may be materials of normal tissues.

The local region may be adjacent to a region where the thickness is estimated.

The estimating of the thickness may be performed by applying a total thickness model obtained by using a continuous thickness phantom image having a combination of two materials.

The total thickness model may have a density of any one of the two materials as a parameter.

The estimating of the thickness may comprise: estimating densities of the two materials; estimating thicknesses of each of the two materials from the radiation image by using the estimated densities and attenuation bases of the two materials; and estimating the thickness of the object by summing the thicknesses of the two materials.

In another general aspect, there is provided an apparatus for processing an image, the apparatus including: a thickness estimating unit to estimate a thickness of an object including at least two materials, from a radiation image taken with radiations of at least two energy bands; and an image generating unit to generate an image by comparing the estimated thickness to a thickness of a local region and extracting a region of interest.

The region of interest may be an abnormal tissue.

The two materials may be materials of normal tissues.

The local region may be adjacent to a region where the thickness is estimated.

The thickness estimating unit may estimate the thickness by applying a total thickness model obtained by using a continuous thickness phantom image having a combination of two materials.

The total thickness model may have a density of any one of the two materials as a parameter.

The thickness estimating unit may estimate densities of the two materials, may estimate thickness of each of the two materials from the radiation image by using the estimated densities and attenuation bases of the two materials, and may estimate the thickness of the object by summing the thicknesses of the two materials.

In another general aspect, there is provided a medical imaging system having an apparatus for processing an image, the apparatus including: a thickness estimating unit to estimate a thickness of an object including at least two materials, from a radiation image taken with radiations of at least two energy bands; and an image generating unit to generate an image by comparing the estimated thickness to a thickness of a local region and extracting a region of interest.

The local region may be adjacent to a region where the thickness is estimated.

The medical imaging system may further include a radiation image obtaining unit to obtain the radiation image by irradiating radiations of at least two energy bands onto the object from the same angle.

The medical imaging system may further include a storage unit to store the generated image, or to store diagnosis information obtained from the generated image.

The medical imaging system may further include a communication unit to transmit the generated image, or transmit diagnosis information obtained from the generated image.

In another general aspect, there is provided a non-transitory computer-readable medium, the medium storing a program that causes a computer including a processor to perform the method described above.

Other features and aspects may be apparent from the following detailed description, the drawings, and the claims.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Described below are examples of methods and apparatuses for processing an image to obtain a diagnostic image. The diagnostic image may depict the image of an abnormal tissue that is extracted from a multi-energy radiation image that depicts a plurality of mixed materials in the body of a patient.

Also described below are examples of medical imaging systems employing such apparatus.

According to one or more of the examples described hereafter, since a region of interest, such as an abnormal tissue, is extracted from a multi-energy radiation image that depicts a plurality of mixed materials in a portion of a patient's body, a high-resolution diagnostic image may be generated by emphasizing the extracted abnormal tissue. Thus, the accuracy of diagnosis may be increased even when only one radiation image is used for diagnosis.

Correlations between an incident intensity and a transmitted intensity of a radiation image, such as an X-ray image, are now described.

The rate of transmittance of an X-ray through an object differs according to the types of and densities of materials found in the object, as well as an energy band of the X-ray. The incident intensity and the transmitted intensity may be represented as shown in Equation 1.

<Equation 1>

$$I(E) = I_0(E) e^{-\mu(E)\rho x}$$

Here, $I(E)$ represents a transmitted intensity, and $I_0(E)$ represents an incident intensity. $\mu(E)$ represents a mass attenuation coefficient in an energy band E, $\rho$ represents the density of an object, and x represents the thickness of the object. Equation 1 is referred to as the Beer-Lambert law.

Figure 1:
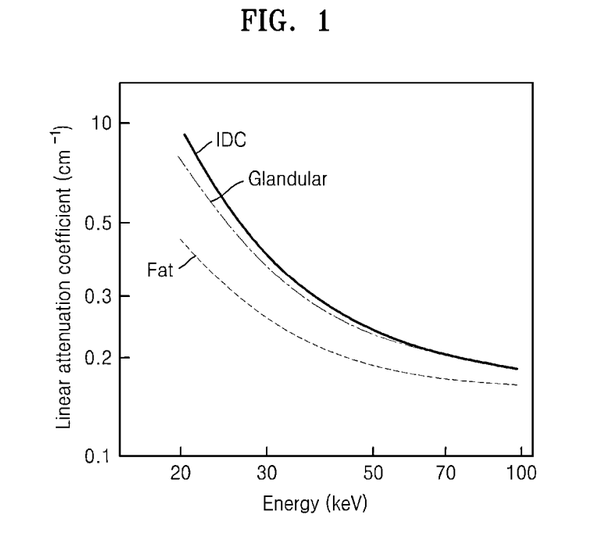
FIG. 1 is a graph illustrating X-ray attenuation coefficients of normal and abnormal body tissues in energy bands.

FIG. 1 illustrates X-ray attenuation coefficients of normal and abnormal body tissues in different energy bands. Referring to FIG. 1, a fat tissue, a glandular tissue, and an infiltrating ductal carcinoma (IDC) tissue have different X-ray attenuation coefficients at different energy bands.

In the case where a radiation, such as an X-ray, is used to scan an object at least two energy bands, energy band images $I_1$ through $I_n$ (n is the number of energy bands) may be obtained. The energy band images $I_1$ through $I_n$ form one radiation image mathematically represented as shown in Equation 2.

<Equation 2>

$$\begin{pmatrix} I_1 \\ I_1 \\ \vdots \\ I_N \end{pmatrix} = \begin{pmatrix} \int_E w_1(E) \left( \exp\left(-\sum_i C_i \mu_i(E)\right) \right) dE \\ \int_E w_2(E) \left( \exp\left(-\sum_i C_i \mu_i(E)\right) \right) dE \\ \vdots \\ \int_E w_N(E) \left( \exp\left(-\sum_i C_i \mu_i(E)\right) \right) dE \end{pmatrix}$$

Here, $w_n$ is an incident intensity of an X-ray in the n-th energy band, and $C_i$ satisfies $C_i = \int_L c_i(r) dr$ and $c_i(r)$ represents a material density projection at each position vector r.

In Equation 2, if the energy band images $I_1$ through $I_n$ are obtained, normal and abnormal body materials in a patient's body may be separated by calculating the material density projection from each of the energy band images $I_1$ through $I_n$.

Meanwhile, since the number of attenuation bases of body constituent materials is two (i.e., photoelectric absorption and Compton scattering), if the maximum number of mixed materials is two, the materials may be separated.

Figure 2:
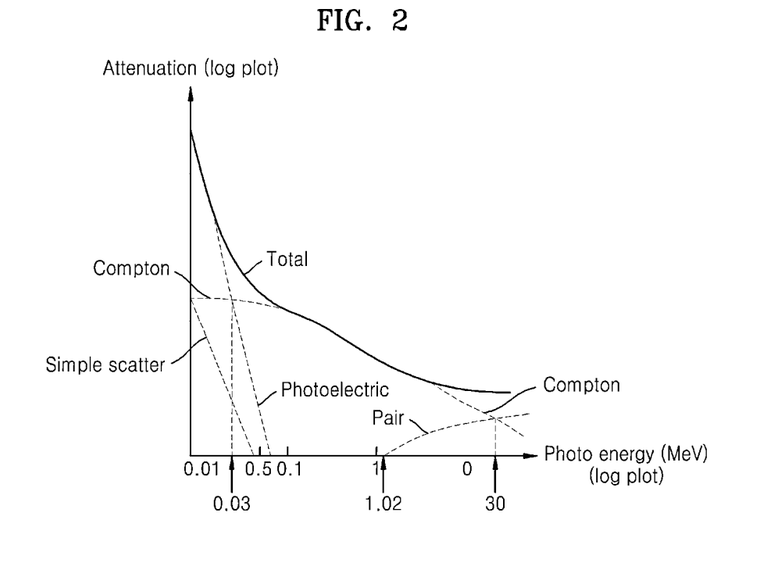
FIG. 2 is a graph illustrating an attenuation basis model of a body constituent material.

FIG. 2 is a graph illustrating an attenuation basis model of a body constituent material, for example, water. Referring to FIG. 2, a physical model may be represented as shown in Equation 3.

<Equation 3>

$$\mu(E, \vec{r}) = c_1(\vec{r}) f_{ph}(E) + c_2(\vec{r}) f_{Co}(E)$$

Meanwhile, an experimental model may be represented as shown in Equation 4.

<Equation 4>

$$\mu(E, \vec{r}) = c_1(\vec{r}) \mu_{water}(E) + c_2(\vec{r}) \mu_{bon}$$

In Equations 3 and 4, $\mu(E, \vec{r})$ represents an attenuation coefficient of a position vector r in an energy band E, $c_1(\vec{r})$ and $c_2(\vec{r})$ represent lengths (thicknesses) of the position vector r of tissues, $f_{ph}(E)$ and $f_{Co}(E)$ and represent basis functions, i.e., attenuation coefficients, according to photoelectric absorption and Compton scattering in the energy band E, and $\mu_{water}(E)$ and $\mu_{bon}$ respectively represent attenuation coefficients of water and bone in the energy band E.

Meanwhile, normal tissues of, for example, a breast from among organs of a body may mainly include an adipose tissue and a glandular tissue. If an abnormal tissue such as a mass tissue is mixed, a total of three materials may be included in a multi-energy radiation image. In this example, three materials may be separated from each other by using the overall thickness information of the object, which is a breast in this case, and the attenuation bases of body constituent materials determined through, i.e., photoelectric absorption and Compton scattering.

For example, if attenuation bases of body constituent materials, i.e., photoelectric absorption and Compton scattering, are used, an attenuation coefficient $\mu(E, \vec{r})$ of a position vector r in an energy band E may be represented as shown in Equation 5.

<Equation 5>

$$\mu(E, \vec{r}) = c_1(\vec{r}) \mu_A + c_2(\vec{r}) \mu_G + c_3(\vec{r}) \mu_C$$
$$= \alpha f_{ph}(E) + \beta f_{Co}(E)$$

Thus, three different materials, including, for example, an adipose tissue A, a glandular tissue G, and an abnormal tissue C such as a cancerous tissue, may not be separated from one another. In this example, $c_1(\vec{r})$, $c_2(\vec{r})$, and $c_3(\vec{r})$ are proportional constants representing thicknesses of tissues, $\mu_A$, $\mu_G$, and $\mu_C$ represent attenuation coefficients of the adipose tissue A, the glandular tissue G, and the abnormal tissue C. $\alpha$ and $\beta$ represent proportional constants, $f_{ph}(E)$ represents a basis function, i.e., an attenuation coefficient, according to photoelectric absorption in an energy band E, and $f_{Co}(E)$ represents a basis function, i.e., an attenuation coefficient, according to Compton scattering in the energy band E.

Meanwhile, a total thickness T of an object may be represented as shown in Equation 6.

<Equation 6>

$$c_1(\vec{r})+c_2(\vec{r})+c_3(\vec{r})=T$$

If the total thickness T of the object is used, an attenuation coefficient $\mu(E,\vec{r})$ of a position vector r in an energy band E may be represented as shown in Equation 7.

<Equation 7>

$$\mu(E,\vec{r})=c_1(\vec{r})(\mu_A-\mu_C)+c_2(\vec{r})(\mu_G-\mu_C)+T\mu_C$$

Thus, three materials may be separated.

Figure 3:
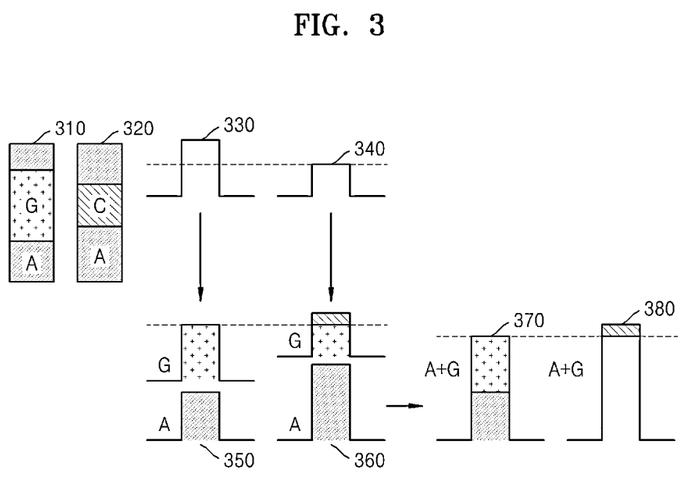
FIG. 3 is a diagram illustrating an example of a method of separating three materials based on information regarding a thickness of an object.

FIG. 3 illustrates an example of a method of separating three different materials present in an object by using information regarding a total thickness of the object. The method may rely on the fact that a total thickness of a body part such as, for example, a compressed breast, is almost constant. For example, a glandular tissue G and an adipose tissue A captured in a radiation image may be separated from one another by using attenuation bases of normal materials such as the glandular tissue G and the adipose tissue A. If the separated glandular tissue G and the adipose tissue A are combined, a total thickness image may be obtained. That is, in a normal region, the total thickness image has the same thickness as a total thickness of the depicted object, i.e., a breast of a patient; however, in an abnormal region, the calculated total thickness image is different from the calculated thickness of the normal region.

Referring to FIG. 3, if a region 310 including an adipose tissue A and a glandular tissue G, and a region 320 including the adipose tissue A, the glandular tissue G, and an abnormal tissue C such as a cancerous tissue respectively have a grayscale intensity 330 and a grayscale intensity 340, the adipose tissue A and the glandular tissue G may be separated from each of the grayscale intensity 330 and the grayscale intensity 340 by using attenuation bases of the adipose tissue A and the glandular tissue G. A thickness 350 represents the adipose tissue A and the glandular tissue G separated from the grayscale intensity 330, and a thickness 360 represents the adipose tissue A and the glandular tissue G separated from the grayscale intensity 340. As described above, if the separated glandular tissue G and the adipose tissue A are combined, the region 310 may have a thickness 370 that is the same as a total thickness of a breast. Thus, the region 310 may be determined as a normal region. However, the region 320 has a calculated thickness 380 that is different from the total thickness of the breast; thus, the region 320 may be determined as an abnormal region.

Figure 4:
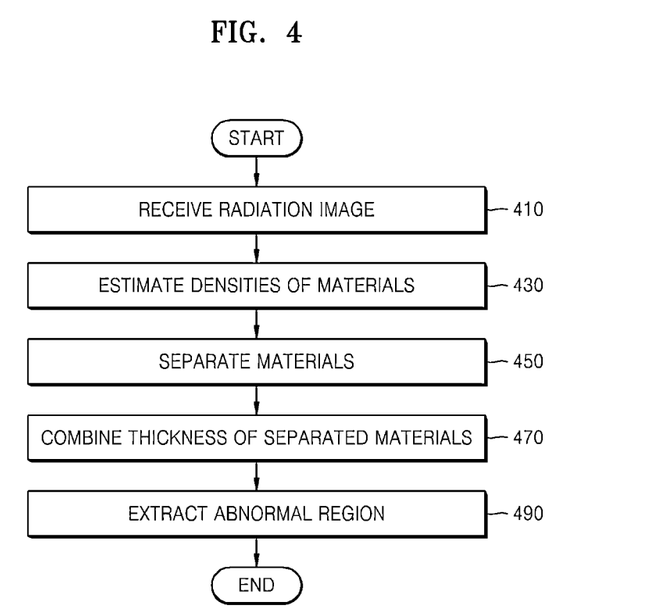
FIG. 4 is a flowchart illustrating an example of a method of processing an image.

FIG. 4 is a flowchart illustrating an example of a method of processing an image according to a general aspect.

Referring to FIG. 4, in operation 410, a multi-energy radiation image taken with a radiation having at least two energy bands of a predetermined subject, such as a body part of a patient, may be received.

In operation 430, the densities of at least two materials included in the multi-energy radiation image may be estimated.

In operation 450, the two materials such as a glandular tissue and an adipose tissue may be separated from the multi-energy radiation image by using the estimated densities of the materials and attenuation bases of the materials.

In operation 470, a total thickness of a region of the body part may be estimated by combining the estimated thickness of the separated glandular tissue and the adipose tissue at the region. Further, although not shown in FIG. 4, in some examples, a uniformity level of the thickness of the body part may be measured by using information regarding the combined thickness estimated in operation 470. In addition, parameters such as the densities of the materials may be updated based on the measured uniformity level and then may be fed back to operation 430.

In operation 490, an abnormal region having an abnormal tissue, such as a mass or microcalcification tissue, may be extracted by comparing the combined thickness to a thickness calculated at a local region of the multi-energy radiation image. A diagnostic image may be generated based on using the information about the extracted abnormal region.

Meanwhile, a total thickness image may be obtained by substituting a total thickness model for operations 430, 450, and 470, representing the total thickness model as a polynomial having a certain number of parameters, and optimizing each parameter to maximize the uniformity of a total thickness. In this example, a total thickness model represented as a linear polynomial may be represented as shown in Polynomial 8.

<Polynomial 8>

$$a_1 I_L + a_2 I_H + a_3$$

A total thickness model represented as a quadratic polynomial may be represented as shown in Polynomial 9.

<Polynomial 9>

$$a_1 I_L + a_2 I_H + a_3 + a_4 I_L^2 + a_6 I_L I_H$$

In Polynomials 8 and 9, $I_L$ and $I_H$ represent a radiation image of a low energy band and a radiation image of a high energy band, respectively and $a_1$, $a_2$, $a_3$, $a_4$, $a_5$, and $a_6$ represent optimized proportional constants.

Figure 5:
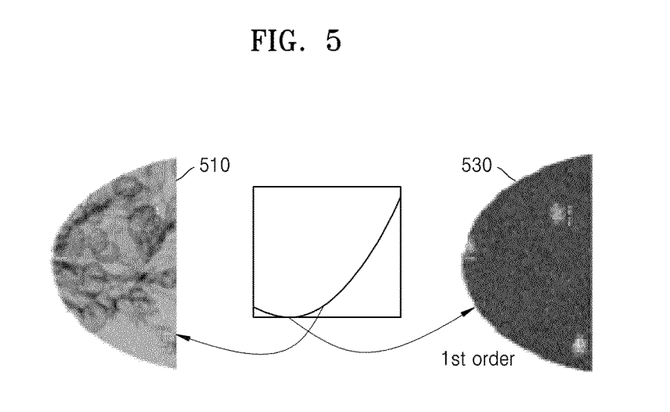
FIG. 5 is a diagram illustrating an example of a method of maximizing uniformity of a thickness of a breast by using a total variation.

FIG. 5 illustrates an example of a method of maximizing uniformity of a total thickness of a breast by using a total variation. Referring to FIG. 5, if a linear polynomial image 530 may be represented by minimizing a total variation L1-norm of a radiation image 510 of the breast, the uniformity of the total thickness of the breast may be maximized.

Meanwhile, a total thickness of a body part, i.e., the breast, may be approximated by using a polynomial, for example, Polynomial 8 or Polynomial 9. In this example, if the order of the polynomial is high, the accuracy of approximation may be increased while the capability of convergence may be reduced because a plurality of parameters should be optimized. Accordingly, a total thickness model having a high accuracy of approximation and a small number of parameters needs to be set. For this, a total thickness model having one parameter may be set by using a continuous thickness phantom image having a combination of two materials.

Figure 6:
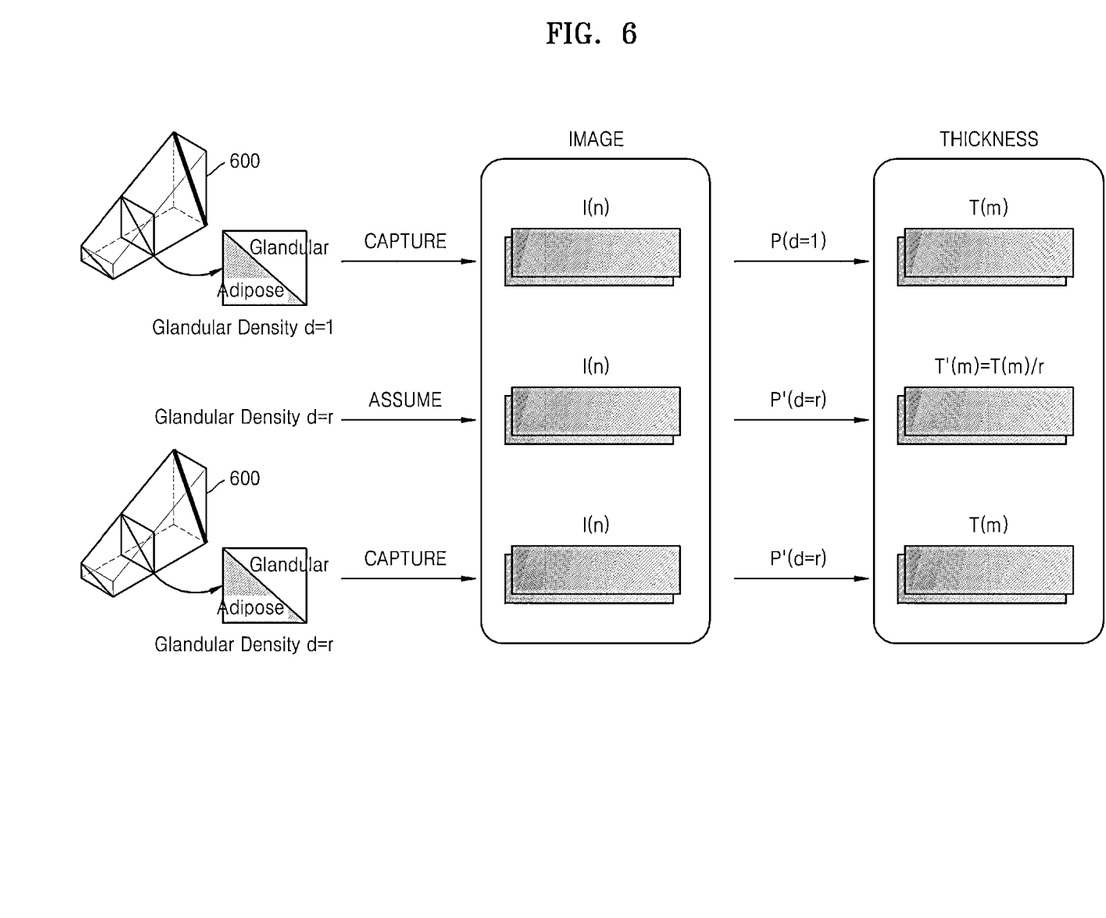
FIG. 6 is a conceptual diagram illustrating an example of a method of setting a total thickness model having one parameter by using a continuous thickness phantom image having a combination of two materials.

FIG. 6 is a conceptual diagram illustrating a method of setting a total thickness model having one parameter by using a continuous thickness phantom image having a combination of two materials.

Referring to FIG. 6, main constituent materials of a body part, for example, a breast, may be an adipose tissue and a glandular tissue, and the density of each tissue may differ according to an individual person. In order to calculate a total thickness model capable of reflecting the difference in density, initially, a continuous thickness phantom image 600 having an average reference density of any one material, for example, the glandular tissue may be captured, and a phantom image I(n) of each energy band and a thickness image T(m) corresponding to the phantom image I(n) may be obtained. Then, it is assumed that the phantom image I(n) is obtained when a density d of the glandular tissue has a certain value, i.e., an average reference density r, and a thickness image T'(m) corresponding to the phantom image I(n) is obtained. In this example, T'(m)=T(m)/r. If an approximation polynomial coefficient between the phantom image I(n) and the thickness image T'(m) is P', the approximation polynomial coefficient P' will be almost identical to a polynomial coefficient by using a phantom image actually captured from a portion where the density d of the glandular tissue is r and a thickness image corresponding to the phantom image. Accordingly, a polynomial coefficient at an arbitrary density of the glandular tissue may be calculated by using one phantom image having an average reference density without capturing a phantom image at every density of the glandular tissue.

Consequently, a total thickness of an object may be represented by using one parameter such as the density d, and may be applied to a polynomial model shown in Polynomials 8 and 9. That is, if the total thickness of the object is f(x), approximation may be performed as f(x)=Polynomial 8, or f(x)=Polynomial 9.

Figure 7:
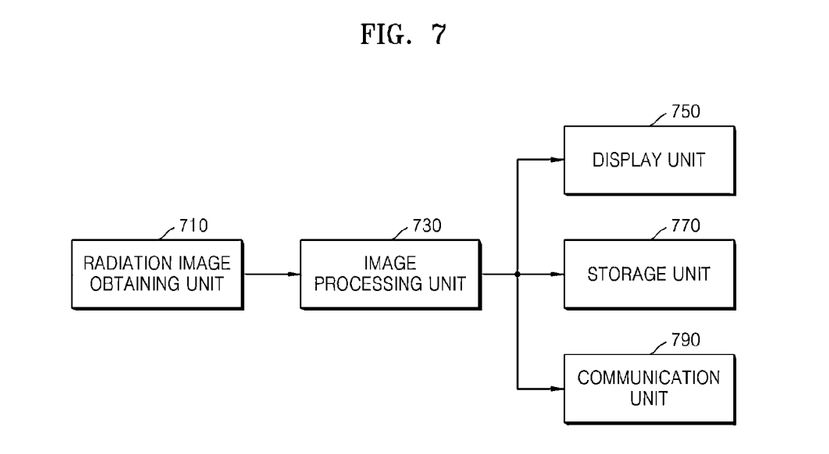
FIG. 7 is a block diagram illustrating an example of a medical imaging system according to a general aspect.

FIG. 7 illustrates an example of a medical imaging system according to a general aspect. The medical imaging system may include a radiation image obtaining unit 710, an image processing unit 730, a display unit 750, a storage unit 770, and a communication unit 90. In this example, the medical imaging system may be implemented by using only the image processing unit 730. That is, the radiation image obtaining unit 710, the display unit 750, the storage unit 770, and the communication unit 790 may be optionally included. Meanwhile, the image processing unit 730 may be implemented as at least one processor.

Referring to FIG. 7, the radiation image obtaining unit 710 may be configured to irradiate a radiation having at least two different energy bands onto an object and to capture a multi-energy radiation image of the object. If a radiation, for example, an X-ray, having different energy bands is irradiated onto the same tissue of a patient, the radiation may be absorbed or scattered by the tissue to different degrees. By using this property, a multi-energy radiation image to which different absorption properties according to energy bands are reflected may be obtained by irradiating an X-ray having two or more energy bands onto each tissue.

Meanwhile, if the radiation image obtaining unit 710 may not be included in the medical imaging system, a multi-energy radiation image provided from outside the medical imaging system may be input to the image processing unit 730.

The image processing unit 730 may extract an abnormal tissue by comparing a total thickness of an object in the multi-energy radiation image provided from the radiation image obtaining unit 710 or outside the medical imaging system, to a thickness calculated at a local region of the multi-energy radiation image, and generate a diagnostic image including the extracted abnormal tissue. That is, normal tissues may be removed from the diagnostic image generated by the image processing unit 730. Meanwhile, the image processing unit 730 may perform noise reduction on the multi-energy radiation image, or may perform noise reduction and/or contrast enhancement on the diagnostic image. Meanwhile, the image processing unit 730 may also have an image reading function, and thus may obtain required diagnosis information from the diagnostic image.

The display unit 750 may be implemented as, for example, a monitor, and may display the diagnostic image generated by the image processing unit 730, or may display the diagnosis information obtained by the image processing unit 730 together with the diagnostic image.

The storage unit 770 may be implemented as, for example, a non-transitory memory, and may store the diagnostic image generated by the image processing unit 730, or may store the diagnosis information obtained by the image processing unit 730, in correspondence with the diagnostic image.

The communication unit 790 may transmit by a wired or wireless network the diagnostic image generated by the image processing unit 730, or the diagnostic image combined with the diagnosis information to another medical imaging system located at a remote place or a specialist such as a doctor at a hospital, and may receive and input the multi-energy radiation image provided from outside the medical imaging system, to the image processing unit 730. In particular, the communication unit 790 may transmit by a wired or wireless network the diagnostic image, or the diagnostic image combined with the diagnosis information to another medical imaging system or a specialist who has transmitted the multi-energy radiation image.

Meanwhile, the storage unit 770 and the communication unit 790 may be integrated into a picture archiving communication system (PACS) by adding image reading and searching functions.

Alternatively, the image processing unit 730, the storage unit 770, and the communication unit 790 may be integrated into a PACS.

Meanwhile, the medical imaging system may be any image diagnostic system using a radiation, for example, an X-ray. For example, the medical imaging system 700 may be a mammographic image diagnostic system used to determine a lesion of breasts including only soft tissues without any bone in a body.

Figure 8:
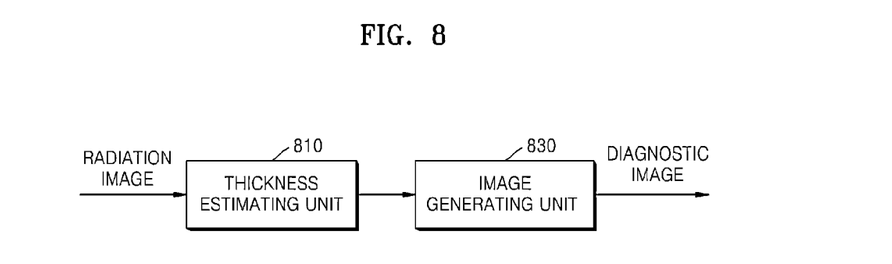
FIG. 8 is a block diagram illustrating an example of an apparatus for processing an image.

FIG. 8 illustrates an example of an apparatus for processing an image according to a general aspect. The image processing apparatus may include a thickness estimating unit 810 and an image generating unit 830. In this example, the thickness estimating unit 810 and the image generating unit 830 may be implemented as at least one processor.

Referring to FIG. 8, the thickness estimating unit 810 may estimate a total thickness of an object from an input multi-energy radiation image. In this example, the total thickness may be estimated by using a continuous thickness phantom image having a combination of two materials, a total thickness model having a density of any one of the two materials as a parameter may be applied to the multi-energy radiation image.

The image generating unit 830 may compare the total thickness estimated by the thickness estimating unit 810 to a thickness calculated at a local region of the multi-energy radiation image, may extract a region of interest, e.g., an abnormal tissue, according to a comparison result, and may generate a diagnostic image including the extracted abnormal tissue.

As described above, according to one or more of the above examples, since a region of interest, e.g., an abnormal tissue, is extracted from a multi-energy radiation image in which a plurality of materials are mixed, and a high-resolution diagnostic image may be generated by emphasizing the extracted abnormal tissue, the accuracy of diagnosis may be increased even when only one radiation image is used.

As described above, according to one or more of the above examples, a method of processing an image is provided. The method includes estimating a total thickness of an object including at least two materials, from a radiation image, that is images taken from one position, obtained with radiations of at least two energy bands and obtained from the same object; and generating a diagnostic image by comparing the estimated total thickness to a thickness of a local region of the radiation image, and extracting a region of interest according to a comparison result. The region of interest may be an abnormal tissue. The two materials may be materials of normal tissues.

The estimating of the total thickness may be performed by applying a total thickness model obtained by using a continuous thickness phantom image having a combination of two materials. The total thickness model may have a density of any one of the two materials as a parameter.

The estimating of the total thickness may include estimating densities of the two materials; separating the two materials from the multi-energy radiation image by using the estimated densities and attenuation bases of the two materials; and estimating the total thickness of the object by summing thicknesses of the two separated materials.

According to another example, an apparatus for processing an image is provided. The apparatus includes a thickness estimating unit to estimate a total thickness of an object including at least two materials, from a radiation image taken with radiations having at least two energy bands; and an image generating unit to generate a diagnostic image by comparing the estimated total thickness to a thickness of a local region, and extracting a region of interest according to a comparison result.

According to still another example, a medical imaging system is provided. The system includes an apparatus for processing an image, the apparatus including a thickness estimating unit to estimate a total thickness of an object that includes at least two materials, from a radiation image taken with radiations of at least two energy bands and obtained from the same object; and an image generating unit to generate a diagnostic image by comparing the estimated total thickness to a thickness of a local region of the radiation image, and extracting a region of interest according to a comparison result.

The medical imaging system may further include a radiation image obtaining unit to obtain the radiation image by irradiating a radiation having at least two energy bands onto the object.

The medical imaging system may further include a storage unit to store the generated diagnostic image, or to store diagnosis information obtained from the generated diagnostic image, in correspondence with the diagnostic image.

The medical imaging system may further include a communication unit to transmit the generated diagnostic image, or transmit diagnosis information obtained from the generated diagnostic image, in correspondence with the diagnostic image.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of non-transitory computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the examples disclosed herein can be easily construed by programmers skilled in the art to which the examples pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of processing an image, the method comprising:
   estimating a thickness of an object that includes at least two materials, from a radiation image taken with radiations of at least two energy bands; and
   generating an image by comparing the estimated thickness to a thickness of a local region and extracting a region of interest;
   wherein the estimating of the thickness is performed by applying a total thickness model obtained by using a continuous thickness phantom image having a combination of two materials.

2. The method of claim 1, wherein the region of interest is an abnormal tissue.

3. The method of claim 2, wherein the two materials are materials of normal tissues.

4. The method of claim 1, wherein the local region is adjacent to a region where the thickness is estimated.

5. The method of claim 1, wherein the total thickness model has a density of any one of the two materials as a parameter.

6. The method of claim 1, wherein the estimating of the thickness comprises:
   estimating densities of the two materials;
   estimating thicknesses of each of the two materials from the radiation image by using the estimated densities and attenuation bases of the two materials; and
   estimating the thickness of the object by summing the thicknesses of the two materials.

7. A non-transitory computer-readable medium, the medium storing a program that causes a computer including a processor to perform the method of claim 1.

8. An apparatus for processing an image, the apparatus comprising:
- a thickness estimating unit configured to estimate a thickness of an object including at least two materials, from a radiation image taken with radiations of at least two energy bands; and
- an image generating unit configured to generate an image by comparing the estimated thickness to a thickness of a local region and extracting a region of interest;
- wherein the thickness estimating unit estimates the thickness by applying a total thickness model obtained by using a continuous thickness phantom image having a combination of two materials.

9. The apparatus of claim 8, wherein the region of interest is an abnormal tissue.

10. The apparatus of claim 9, wherein the two materials are materials of normal tissues.

11. The apparatus of claim 8, wherein the local region is adjacent to a region where the thickness is estimated.

12. The apparatus of claim 8, wherein the total thickness model has a density of any one of the two materials as a parameter.

13. The apparatus of claim 8, wherein the thickness estimating unit estimates densities of the two materials, estimates thickness of each of the two materials from the radiation image by using the estimated densities and attenuation bases of the two materials, and estimates the thickness of the object by summing the thicknesses of the two materials.

14. A medical imaging apparatus for processing an image, the apparatus comprising:
- a thickness estimating unit configured to estimate a thickness of an object including at least two materials, from a radiation image taken with radiations of at least two energy bands; and
- an image generating unit configured to generate an image by comparing the estimated thickness to a thickness of a local region and extracting a region of interest;
- wherein the thickness estimating unit estimates the thickness by applying a total thickness model obtained by using a continuous thickness phantom image having a combination of two materials.

15. The medical imaging apparatus of claim 14, wherein the local region is adjacent to a region where the thickness is estimated.

16. The medical imaging apparatus of claim 14, further comprising a radiation image obtaining unit configured to obtain the radiation image by irradiating radiations of at least two energy bands onto the object from the same angle.

17. The medical imaging apparatus of claim 14, further comprising a storage unit configured to store the generated image, or configured to store diagnosis information obtained from the generated image.

18. The medical imaging apparatus of claim 14, further comprising a communication unit configured to transmit the generated image, or configured to transmit diagnosis information obtained from the generated image.

* * * * *